(12) United States Patent
Yoshioka et al.

(10) Patent No.: US 11,559,636 B2
(45) Date of Patent: Jan. 24, 2023

(54) WARMING DEVICE AND INFUSION SYSTEM

(71) Applicant: MED-TECH INC., Tokyo (JP)

(72) Inventors: Noriaki Yoshioka, Saitama (JP); Taisuke Funamoto, Saitama (JP)

(73) Assignee: MED-TECH INC., Tokyo (JP)

(*) Notice: Subject to any disclaimer, the term of this patent is extended or adjusted under 35 U.S.C. 154(b) by 567 days.

(21) Appl. No.: 16/343,585

(22) PCT Filed: Sep. 27, 2017

(86) PCT No.: PCT/JP2017/034982
§ 371 (c)(1),
(2) Date: Apr. 19, 2019

(87) PCT Pub. No.: WO2018/074165
PCT Pub. Date: Apr. 26, 2018

(65) Prior Publication Data
US 2020/0046914 A1   Feb. 13, 2020

(30) Foreign Application Priority Data

Oct. 21, 2016  (JP) .............................. JP2016-206892
Oct. 21, 2016  (JP) .............................. JP2016-206898

(51) Int. Cl.
*A61M 5/44* (2006.01)
*A61M 5/14* (2006.01)
(Continued)

(52) U.S. Cl.
CPC ................ *A61M 5/44* (2013.01); *A61M 5/14* (2013.01); *H05B 3/20* (2013.01); *H05B 3/54* (2013.01)

(58) Field of Classification Search
CPC ...... A61M 5/44; A61M 5/14; A61M 2205/36; A61M 2205/3673; H05B 3/20; H05B 3/54; H05B 3/78
See application file for complete search history.

(56) References Cited

U.S. PATENT DOCUMENTS

| | | | |
|---|---|---|---|
| 5,245,693 A * | 9/1993 | Ford ........................ | A61M 5/44 165/169 |
| 5,381,510 A * | 1/1995 | Ford ........................ | H05B 3/36 165/169 |
| 6,142,974 A * | 11/2000 | Kistner ................... | F28D 7/0091 604/113 |

(Continued)

FOREIGN PATENT DOCUMENTS

| | | |
|---|---|---|
| CN | 1205072 A | 1/1999 |
| GB | 2101966 | 1/1983 |

(Continued)

OTHER PUBLICATIONS

Translated description of the foreign patent JP-2015157041-A (Year: 2015).*
Official Communications issued in International Bureau of WIPO Patent Application No. PCT/JP2017/034982, dated Nov. 28, 2017, along with English language translations.

*Primary Examiner* — Kami A Bosworth
*Assistant Examiner* — Antarius S Daniel
(74) *Attorney, Agent, or Firm* — Greenblum & Bernstein, P.L.C.

(57) ABSTRACT

Provided is a warming device which can efficiently warm a blood product and inhibit a liquid in a warming flow path from exceeding an upper limit temperature thereof when liquid delivery of the blood product is stopped. The warming device includes the warming flow path in which the blood product flows and a heat plate which is in contact with the warming flow path to supply heat to the warming flow path.

(Continued)

On the heat plate, a heater in a predetermined pattern corresponding to the warming flow path is disposed. The heater is disposed such that an amount of heat generation toward the warming flow path decreases in stages from an upstream side toward a downstream side in the warming flow path and that a decrease rate of the amount of heat generation at each of the stages decreases from the upstream side toward the downstream side.

17 Claims, 18 Drawing Sheets

(51) Int. Cl.
*H05B 3/20* (2006.01)
*H05B 3/54* (2006.01)

(56) References Cited

U.S. PATENT DOCUMENTS

| | | |
|---|---|---|
| 2005/0008354 A1 | 1/2005 | Cassidy |
| 2012/0330234 A1 | 12/2012 | Balluff et al. |

FOREIGN PATENT DOCUMENTS

| | | | |
|---|---|---|---|
| JP | 56-013386 | | 2/1981 |
| JP | S57-192565 | | 11/1982 |
| JP | 9-500481 | | 1/1997 |
| JP | 2002-146540 A | | 5/2002 |
| JP | 2002-526198 | | 8/2002 |
| JP | 2007-527495 | | 9/2007 |
| JP | 2015-073848 | | 4/2015 |
| JP | 2015-157041 | | 9/2015 |
| JP | 2015157041 A | * | 9/2015 |

* cited by examiner

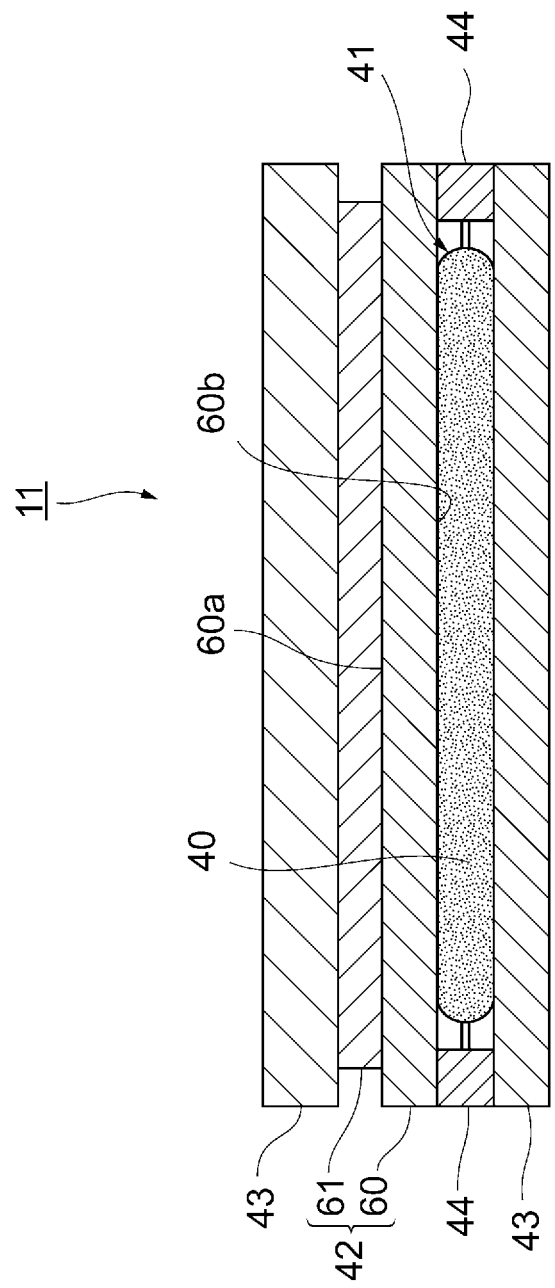

WARMING DEVICE AND INFUSION SYSTEM

TECHNICAL FIELD

The present application is based on Japanese Patent Application No. 2016-206892 and Japanese Patent Application No. 2016-206898 each filed on Oct. 21, 2016, the contents of which are incorporated herein by reference.

The present invention relates to a warming device and an infusion system.

BACKGROUND ART

In a hospital, for the purpose of maintaining the function of a blood product to be infused into a patient, the blood product is stored under refrigeration. When a blood product is infused into a patient, to reduce a burden on the patient, the blood product may be warmed to an appropriate temperature and then infused. In particular, in the event of major or fatal bleeding, a blood product needs to be infused in large amounts in a short time. At this time, to prevent hypothermia, the blood product needs to be rapidly warmed to the body temperature of the patient.

Conventionally, for use in treating a patient who had the major or fatal bleeding mentioned above, an infusion system has been known in which a blood product is infused into the patient, while being warmed. There is an infusion system in which a blood product is caused to flow in a warming flow path, while the warming flow path is heated with a heat plate having a heater (see Patent Document 1).

In the infusion system mentioned above, to rapidly warm a low-temperature blood product, the blood product needs to be efficiently warmed. To satisfy the need, it can be considered to, e.g., increase the temperature of the heater and produce a large temperature difference between the heat plate and the blood product. However, when heated to a high temperature, the blood product results in morphological or functional abnormality or hemolysis. Accordingly, there is an upper limit temperature which allows the blood product to be held (in a preferable state) without resulting in abnormality or hemolysis. The upper limit temperature is about 42° C. so that there is a limit to increasing the temperature of the heater.

To efficiently warm a liquid for which an upper limit temperature is determined, such as a blood product, there is a method in which the power of a heater portion is set higher in the upstream warming section thereof than in the downstream warming section thereof (see Patent Document 2).

CITATION LIST

Patent Document

Patent Document 1: Patent Publication JP-A-2015-073848
Patent Document 2: Patent Publication JP-A-2015-157041

SUMMARY

Technical Problem

However, even when the power of the heater portion is merely set higher in the upstream warming section thereof than in the downstream warming section thereof, there may be a case where the temperature of the heat plate is not satisfactorily increased with respect to the upstream portion of the warming flow path and heating efficiency cannot be sufficiently increased. There may also be a case where, when the liquid delivery of the blood product is stopped in the warming flow path, the heat stored in the heat plate flows into the warming flow path so that the blood product exceeds the upper limit temperature thereof.

The present application has been achieved in view of such a point, and an object of the present application is to provide a warming device and an infusion system which can efficiently warm a liquid to be infused, such as a blood product, and inhibit the liquid in a warming flow path from exceeding the upper limit temperature thereof when the delivery of the liquid is stopped.

Solution to Problem

As a result of conducting vigorous study, the present inventors have found that the above problem can be solved by, e.g., disposing a heater such that an amount of heat generation toward a warming flow path decreases from an upstream side toward a downstream side in a warming flow path and that, when the warming flow path is equally divided into three or more regions along the flow path, a decrease rate of the amount of heat generation decreases from the upstream region toward the downstream region and completed the present invention.

That is, the present invention includes the following aspects.

(1) A warming device which warms a liquid to be infused, including a warming flow path in which the liquid flows, and a heat plate which is in contact with the warming flow path to supply heat to the warming flow path. On the heat plate, a heater in a predetermined pattern corresponding to the warming flow path is disposed, and the heater is disposed such that an amount of heat generation toward the warming flow path decreases in stages from an upstream side toward a downstream side in the warming flow path and that a decrease rate of the amount of heat generation at each of the stages decreases from the upstream side toward the downstream side.

(2) A warming device which warms a liquid to be infused, including a warming flow path in which the liquid flows, and a heat plate which is in contact with the warming flow path to supply heat to the warming flow path. On the heat plate, a heater in a predetermined pattern corresponding to the warming flow path is disposed, and the heater is disposed such that an amount of heat generation toward the warming flow path decreases from an upstream side toward a downstream side in the warming flow path and that, when the warming flow path is equally divided into three or more regions along the flow path, a decrease rate of the amount of heat generation decreases from the upstream region toward the downstream region.

(3) The warming device according to aspect (2), wherein the heater is disposed such that the amount of heat generation exponentially decreases from the upstream side toward the downstream side along the warming flow path.

(4) The warming device according to any one of aspects (1) to (3), wherein the heater is a heating wire.

(5) The warming device according to aspect (4), wherein the amount of heat generation from the heater decreases from the upstream side toward the downstream side in the warming flow path by varying a density of the heating wire.

(6) The warming device according to aspect (4) or (5), wherein the amount of heat generation from the heater decreases from the upstream side toward the downstream side in the warming flow path by varying a resistance of the heating wire.

(7) The warming device according to any one of aspects (1) to (6), wherein, in at least an upstream portion of the warming flow path closer to an inlet port thereof, the heater is disposed along the warming flow path.

(8) The warming device according to any one of aspects (1) to (7), wherein the warming flow path has a structure in which a plurality of reciprocating paths each including an outgoing path and an incoming path are laterally arranged and coupled together, the most upstream reciprocating path of the warming flow path has a plurality of regions along the warming flow path, and the heater is disposed such that the amount of heat generation toward the plurality of regions of the most upstream reciprocating path decreases from the upstream region toward the downstream region.

(9) A warming device which warms a liquid to be infused, including a warming flow path in which the liquid flows, and a heat plate which is in contact with the warming flow path to supply heat to the warming flow path. On the heat plate, a heater in a predetermined pattern corresponding to the warming flow path is disposed, the warming flow path has a structure in which a plurality of reciprocating paths each including an outgoing path and an incoming path are laterally arranged and coupled together, and at least a portion of the heater is disposed along the reciprocating path of the warming flow path.

(10) The warming device according to aspect (9), wherein the heater is disposed along at least the most upstream reciprocating path of the warming flow path.

(11) The warming device according to aspect (9) or (10), wherein at least the most upstream reciprocating path of the warming flow path has a plurality of regions along the warming flow path, and the heater is disposed such that an amount of heat generation toward the plurality of regions of the most upstream reciprocating path decreases from the upstream region toward the downstream region.

(12) The warming device according to any one of aspects (1) to (11), wherein the heat plate is provided with a slit which inhibits heat transmission between respective regions of the heat plate where the adjacent flow paths in the warming flow path are individually disposed.

(13) The warming device according to aspect (12), wherein the heat plate is provided with a slit which inhibits heat transmission between a region of the heat plate where the heater is disposed and another region of the heat plate.

(14) The warming device according to aspect (12), wherein the warming flow path has a structure in which a plurality of reciprocating paths each including an outgoing path and an incoming path are laterally arranged and coupled together, and the slit is provided in a position corresponding to a space between at least one adjacent pair of the outgoing path and the incoming path of the plurality of reciprocating paths.

(15) The warming device according to aspect (14), wherein the slit is provided in a position corresponding to a space between the outgoing path and the incoming path of at least the most upstream reciprocating path of the warming flow path.

(16) The warming device according to aspect (13), wherein, in the other region of the heat plate, at least either one of a non-contact-type temperature sensor which measures a temperature of an inlet portion of the warming flow path and a non-contact-type temperature sensor which measures a temperature of an outlet portion of the warming flow path is provided.

(17) An infusion system including the warming device according to any one of aspects (1) to (16).

Advantageous Effects of Invention

According to the present invention, it is possible to provide a warming device and an infusion system which can efficiently warm a liquid to be infused and inhibit the liquid in a warming flow path from exceeding the upper limit temperature thereof when the delivery of the liquid is stopped.

BRIEF DESCRIPTION OF DRAWINGS

FIG. 18 is an illustrative view showing the outline of a configuration of a warming device when the heater is provided only on one of the surfaces of the warming flow path.

DESCRIPTION OF EMBODIMENTS

Figure 1:
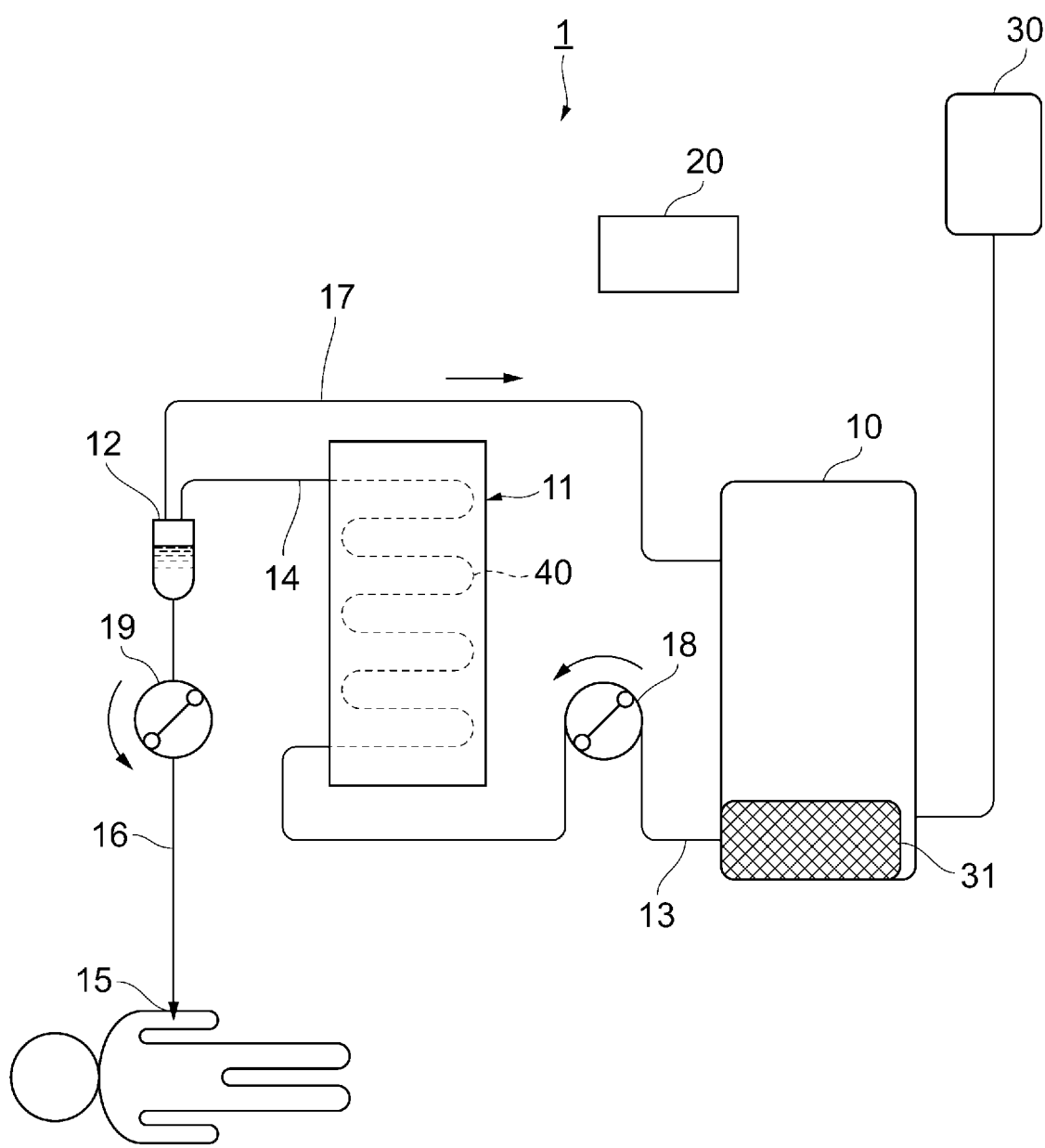
FIG. 1 is a schematic diagram showing the outline of a configuration of an infusion system.

The following will describe preferred embodiments of the present invention with reference to the drawings. Note that the same elements are given the same reference numerals and a repeated description thereof is omitted. It is assumed that the positional relationship among an upper side, a lower side, a left side, and a right sight is based on the positional relationship shown in the drawings unless particularly described otherwise. A dimensional ratio in each of the drawings is not limited to the illustrated ratio. The following embodiments are examples for describing the present invention, and the present invention is not limited to the embodiments.

First Embodiment

FIG. 1 shows an example of a configuration of an infusion system 1. As shown in FIG. 1, the infusion system 1 includes a liquid container 10 which contains a blood product as a liquid to be infused, a warming device 11 which warms the blood product, a bubble removal chamber 12 which removes bubbles in the blood product, a first flow path 13 which connects the liquid container 10 and the warming device 11, a second flow path 14 which connects the warming device 11 and the bubble removal chamber 12, a third flow path 16 which connects the bubble removal chamber 12 and an infusion portion 15 which performs infusion to a patient, a fourth flow path 17 which connects the bubble removal chamber 12 and the liquid container 10, a first pump 18 provided in the first flow path 13, a second pump 19 provided in the third flow path 16, a control device 20, and the like.

The liquid container 10 is connected to, e.g., a liquid bag 30 serving as a source which supplies the blood product. The liquid container 10 is provided with a filter 31 which removes the unneeded component of the blood product that flows out into the first flow path 13. The liquid container 10 is made of, e.g., a resin and has a capacity of, e.g., not less than 0.5 L.

As shown in FIG. 1, to the upper portion of the bubble removal chamber 12, the second flow path 14 and the fourth flow path 17 are connected while, to the lower portion of the bubble removal chamber 12, the third flow path 16 is connected.

The first flow path 13, the second flow path 14, the third flow path 16, and the fourth flow path 17 are formed of soft flexible tubes.

As the first pump 18 and the second pump 19, e.g., tube pumps are used. Each of the first pump 18 and the second pump 19 has a liquid deliverability of, e.g., not less than 100 mUmin, preferably not less than 250 mUmin, and more preferably not less than 500 mUmin. The operation of each of the first pump 18 and the second pump 19 is controlled by the control device 20.

The control device 20 is, e.g., a versatile computer and causes a CPU to execute the program recorded in a memory to control the warming device 11, the first pump 18, the second pump 19, and the like and allows the infusion system 1 to perform an infusing operation.

Figure 2:
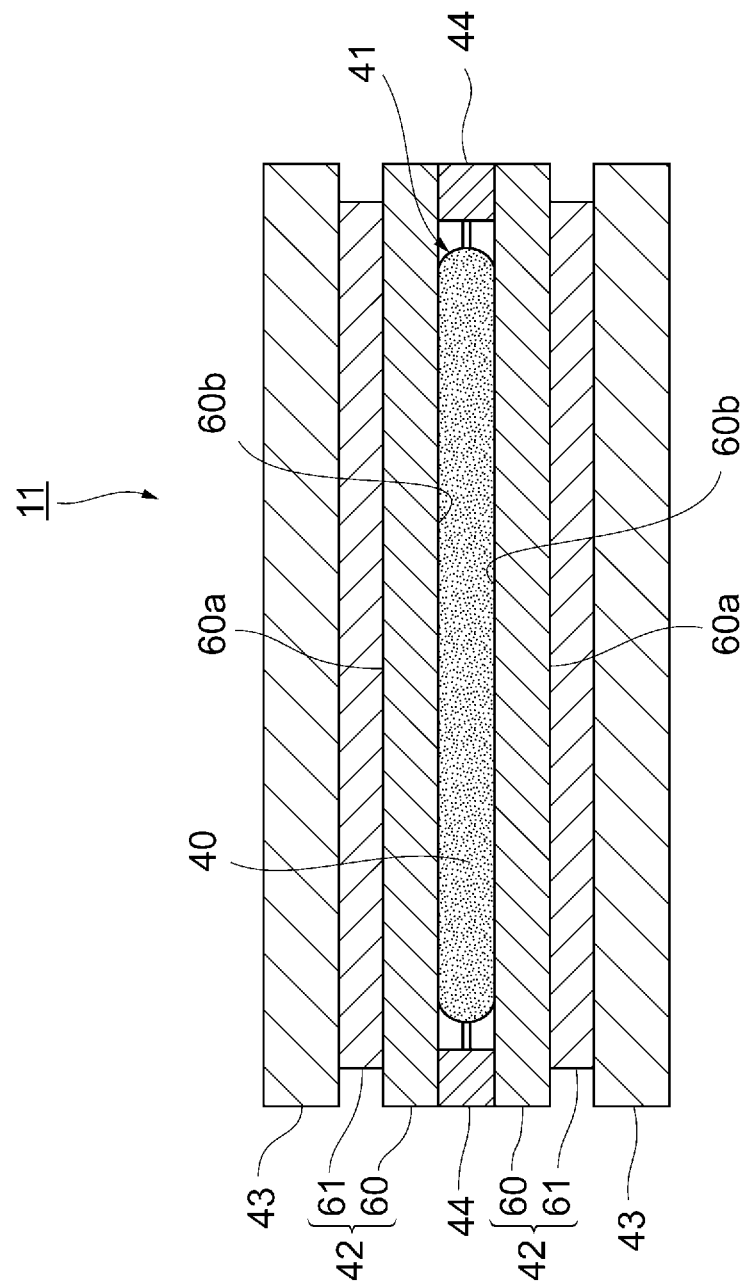
FIG. 2 is an illustrative view showing the outline of a configuration of a warming device.
Figure 3:
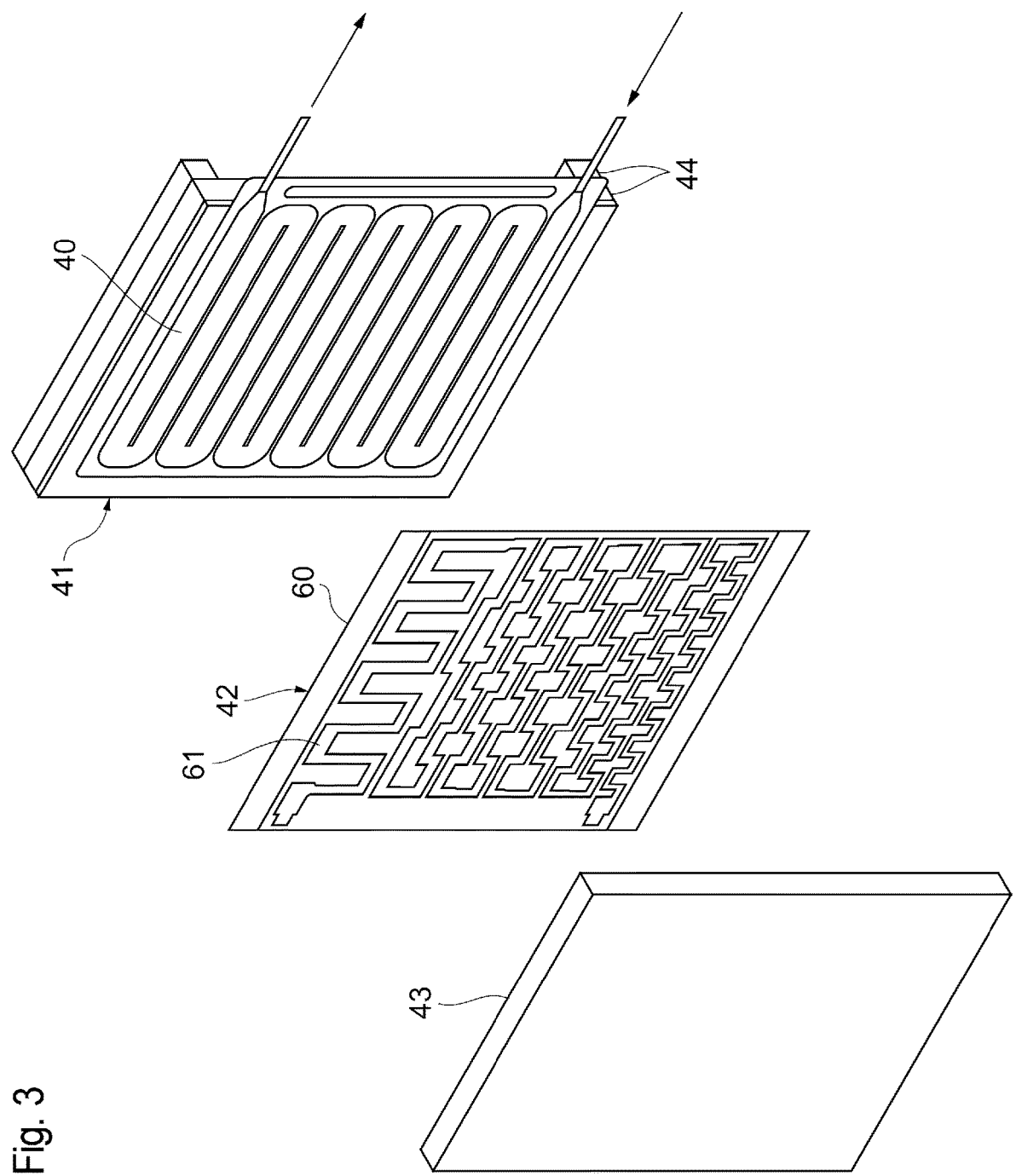
FIG. 3 is a partially exploded view showing the outline of the configuration of the warming device.

As shown in FIGS. 2 and 3, the warming device 11 includes a warming portion 41 having a warming flow path 40 in which the blood product flows, heat supply portions 42 which are in contact with the warming flow path 40 to supply heat, and heat insulating portions 43.

The warming portion 41, the heat supply portions 42, and the heat insulating portions 43 are each formed in a square plate shape and are stacked. At the center of a stacked structure, the warming portion 41 is disposed. On both sides of the warming portion 41, the heat supply portions 42 are disposed, and the heat insulating portions 43 are disposed on the outside thereof. Around the warming portion 41, a spacer 44 for ensuring a space where the warming portion 41 is to be disposed between the heat supply portions 42 on both side thereof is provided.

Figure 4:
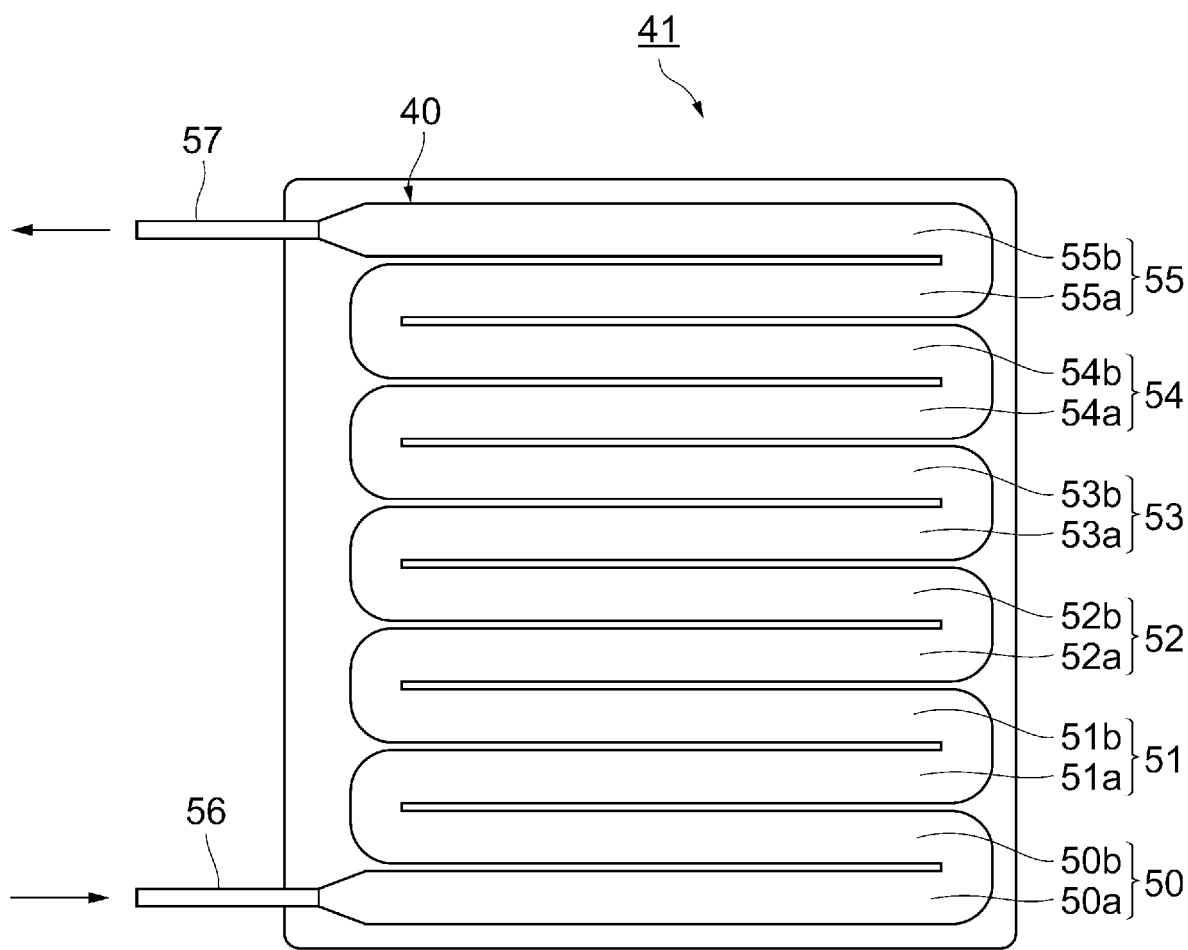
FIG. 4 is a schematic diagram showing the outline of a configuration of a warming portion.

The warming portion 41 is made of a flexible resin and formed in a square plate shape, as shown in FIG. 4. The warming flow path 40 is configured in the form of, e.g., a flexible tube and formed so as to meander in the warming portion 41. Specifically, the warming flow path 40 has a shape in which a plurality of reciprocating paths are laterally arranged and coupled together. In the present embodiment, the warming flow path 40 has, e.g., six reciprocating paths 50, 51, 52, 53, 54, and 55 having substantially equal flow path widths. An inlet portion 56 and an outlet portion 57 of the warming flow path 40 are provided in, e.g., the end portions of the warming portion 41 in the same direction.

The warming flow path 40 has a flow path area of not less than 200 cm$^2$. Note that the "flow path area" is the area of the portion of the warming flow path 40 which is in contact with heat media (heat plates 60). The wall of the tube of the warming flow path 40 has a thickness of not more than 0.4 mm, preferably not more than 0.3 mm, and more preferably not more than 0.2 mm.

As shown in FIGS. 2 and 3, each of the heat supply portions 42 has the heat plate 60 and a heater 61 in a predetermined pattern which generates heat from supplied power. The heat plate 60 is formed in, e.g., the same square plate shape as that of the warming portion 41. The heater 61 is provided on a first surface 60a of the heat plate 60, and the warming flow path 40 is in contact with a second surface 60b of the heat plate 60. As a result, heat from the heater 61 is transmitted to the warming flow path 40 via the heat plate 60.

Figure 5:
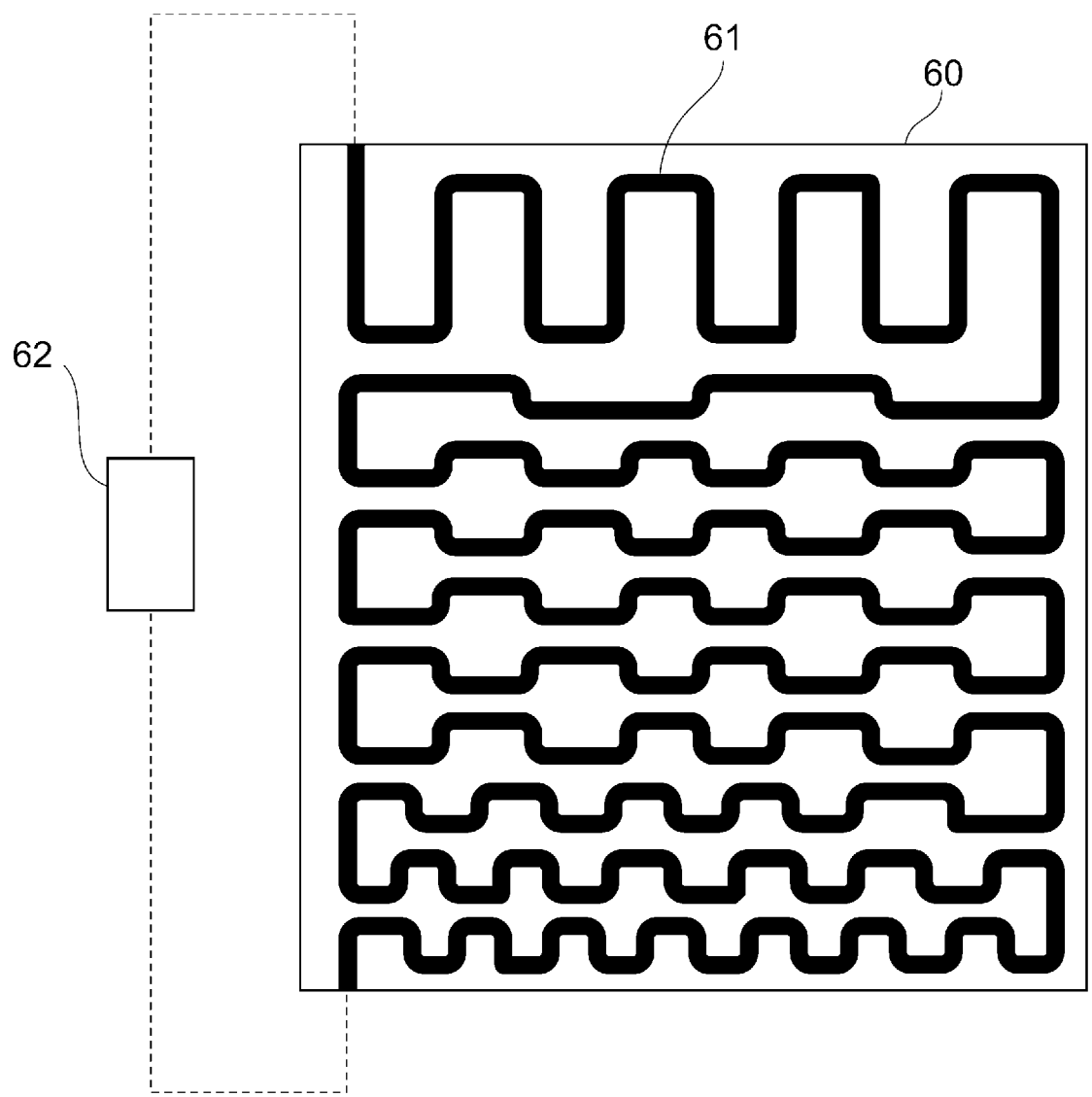
FIG. 5 is an illustrative view showing an example of the pattern of a heater.
Figure 6:
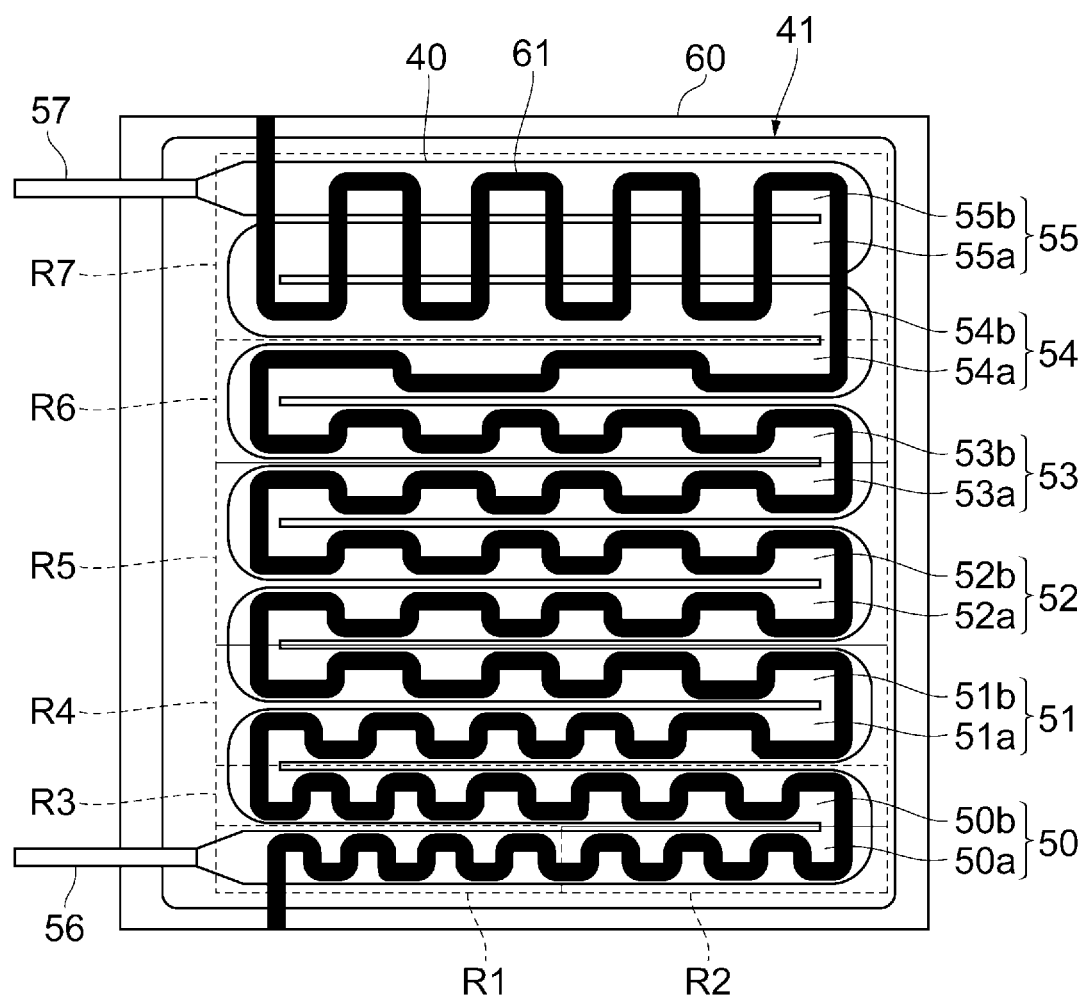
FIG. 6 is an illustrative view showing the positional relationship between a warming flow path and the pattern of the heater.
Figure 7:
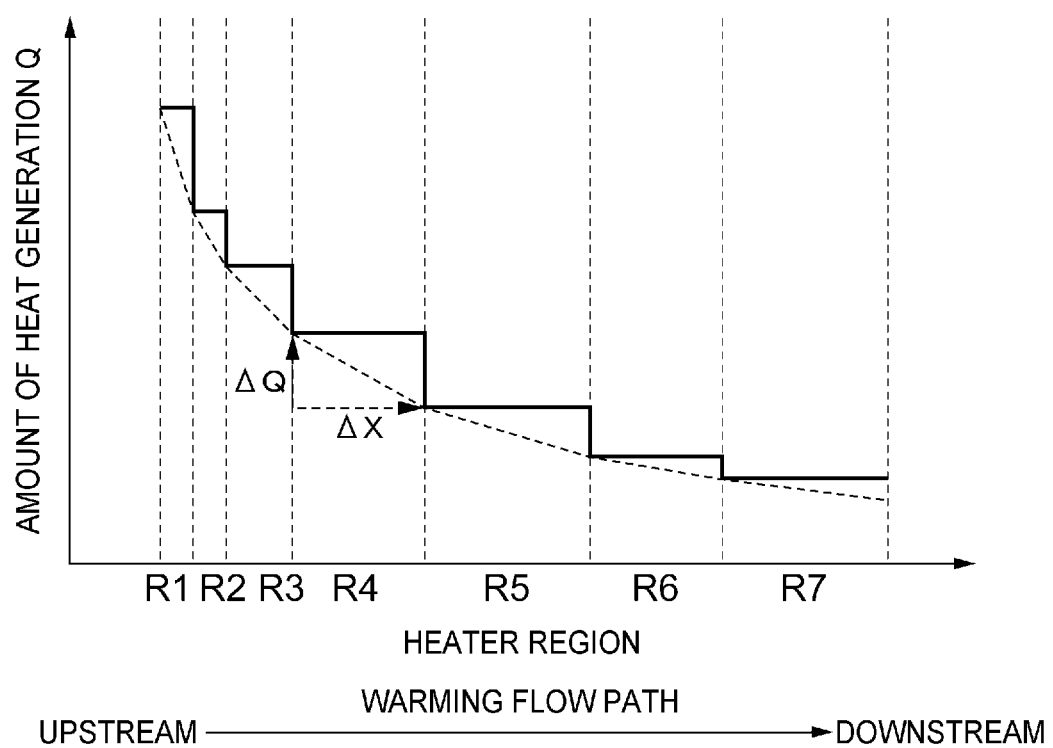
FIG. 7 is a graph showing an example of the relationship between an amount of heat generation from the heater and the warming flow path.

As shown in FIG. 5, each of the heaters 61 is formed in the predetermined pattern on the heat plate 60. The heater 61 is supplied with power from a power supply device 62 to generate heat. As shown in FIG. 6, the heater 61 has the pattern corresponding to the warming flow path 40. As shown in FIG. 7, the heater 61 is disposed such that an amount of heat generation (heater power) Q decreases in stages from an upstream side toward a downstream side in the warming flow path 40 and that a decrease rate (inclination) of the amount of heat generation Q at each of the stages (regions) decreases from the upstream side toward the downstream side. In this case, it is assumed that the decrease rate of the amount of heat generation Q at each of the stages corresponds to the inclination of a straight line obtained by determining the amount of heat generation Q at the upstream end of each of the stages and the amount of heat generation Q at the downstream end of each of the stages (amount of heat generation Q at the upstream end of the subsequent stage) and connecting the determined amounts of heat generation Q. In other words, each of decrease rates A1 to A7 at the individual stages (regions R1 to R7 described later) corresponds to $\Delta Q/\Delta X$ in each of the regions R1 to R7 in FIG. 7 and satisfies the relationship given by $A1>A2>A3>A4>A5>A6>A7$.

Specifically, as shown in FIG. 6, the heater 61 is divided into, e.g., a plurality of regions along the plurality of reciprocating paths 50 to 55 of the warming flow path 40 and disposed such that the amount of heat generation Q decreases in stages from the upstream region toward the downstream region and that the decrease rate of the amount of heat generation Q decreases. The heater 61 is divided into, e.g., the seven regions R1 to R7. For example, the most upstream reciprocating path 50, located close to the inlet portion 56, is divided into the three regions R1 to R3. Of the most upstream reciprocating path 50, an outgoing path 50a is divided into the two regions R1 and R2, while an incoming path 50b is formed of the one region R3. The reciprocating path 51 (including an outgoing path 51a and an incoming path 51b) is formed of the one region R4. The reciprocating path 52 (including an outgoing path 52a and an incoming path 52b) and an outgoing path 53a of the reciprocating path 53 are formed of the one region R5. An incoming path 53b of the reciprocating path 53 and an outgoing path 54a of the reciprocating path 54 are formed of the one region R6, while an incoming path 54b of the reciprocating path 54 and the reciprocating path 55 (including an outgoing path 55a and an incoming path 55b) are formed of the one region R7.

The heater 61 is, e.g., a continuous heating wire. The amount of heat generation Q in each of the regions R1 to R7 is defined by varying at least one of the density and resistance (such as width, thickness, or material) of the heating wire. Note that the heating wire may be either continuous or divided into a plurality of sections.

For example, each of the heaters 61 for the reciprocating paths 50, 51, 52, and 53 and the outgoing path 54a (in the regions R1 to R6) of the reciprocating path 54 is disposed over the warming flow path 40 along the warming flow path 40. The heater 61 in the regions R1 to R6 is provided to extend over the warming flow path 40 from the upstream side toward the downstream side, while meandering in a rectangular shape. The heater 61 in the regions R1 to R6 does not widthwise protrude from the warming flow path 40 when viewed in plan view.

The heater 61 for the incoming path 54b of the reciprocating path 54 and the reciprocating path 55 (in the region R7) meanders in a rectangular shape over the three flow paths. The density of the heating wire of the heater 61 in the regions R1, R2, R3, R4, R5, R6, and R7 gradually decreases in this order. As a result, the amount of heat generation Q toward the warming flow path 40 decreases in stages from the upstream side toward the downstream side. In addition, the decrease rate of the amount of heat generation Q in each of the regions R1 to R7 gradually decreases from the upstream side toward the downstream side. The number of times the heater 61 meanders in the regions R1 to R6 gradually decreases in this order.

Next, a description will be given of the operation of the infusion system 1 thus configured. First, as shown in FIG. 1, the liquid bag 30 storing therein a low-temperature blood product is connected to the liquid container 10 so that the blood product in the liquid bag 30 is stored in the liquid container 10. Then, the first pump 18 and the second pump 19 are activated to deliver the blood product in the liquid container 10 to the warming device 11 through the first flow path 13. In the warming device 11, the blood product passes through the warming flow path 40, while simultaneously being warmed to a predetermined temperature close to a body temperature by the heat plates 60 using the heaters 61 as a heat source.

Figure 8:
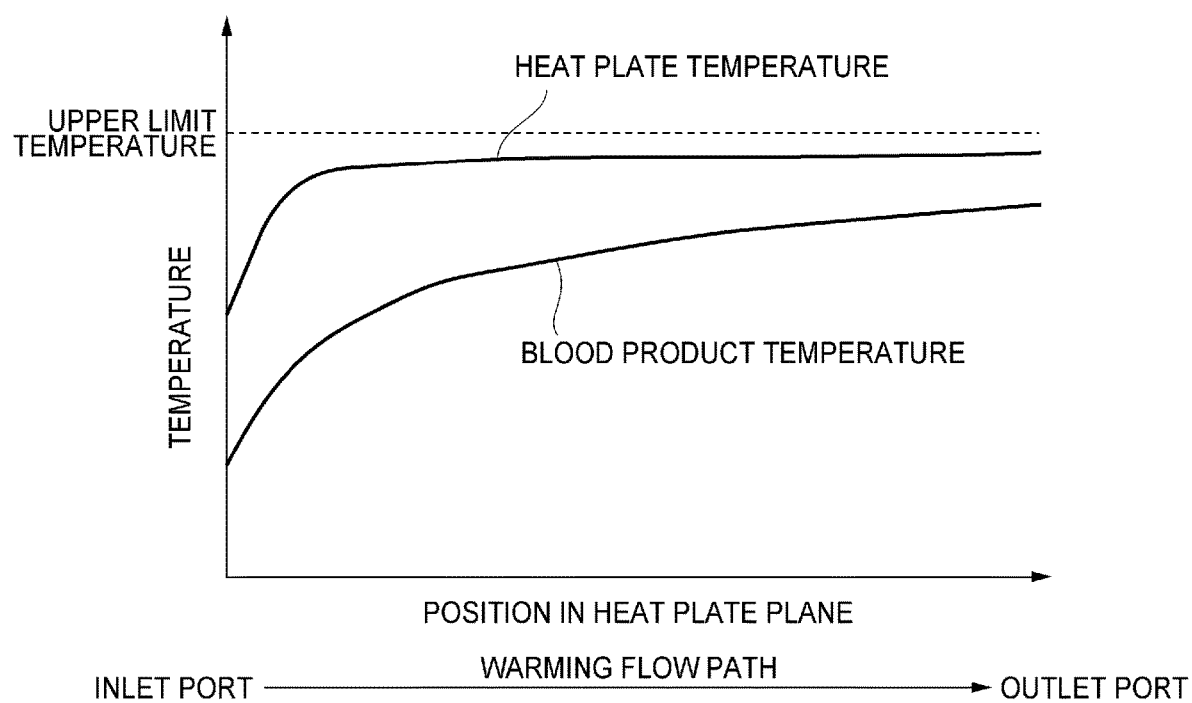
FIG. 8 is a graph showing an example of the temperature of a heat plate.

At this time, the heater 61 gives heat to the heat plate 60 such that, as shown in FIG. 7, the amount of heat generation Q decreases in stages from the upstream side toward the downstream side in the warming flow path 40 and that the decrease rate (AQ/AX) at each of the stages (regions R1 to R7) decreases from the upstream side toward the downstream side. As a result, the in-plane temperature of the heat plate 60 rapidly increases up to a level around the upper limit temperature of the blood product in a position corresponding to the upstream portion of the warming flow path 40, as shown in, e.g., FIG. 8. The temperature is maintained in a direction toward the downstream side in the warming flow path 40 and does not exceed the upper limit temperature of the blood product throughout the entire region of the warming flow path 40. As a result, the blood product passing through the warming flow path 40 has a large temperature difference with the heat plate 60 in the upstream portion of the warming flow path 40, and is therefore efficiently warmed rapidly. Then, the blood product is gradually warmed gently up to an intended temperature in the downstream portion of the warming flow path 40.

The blood product warmed in the warming device 11 passes through the second flow path 14 to flow into the bubble removal chamber 12. Then, the blood product is caused by the second pump 19 to pass through the third flow path 16 to be infused into a patient from the infusion portion 15. The amount of infusion to the patient is controlled by adjusting the liquid delivery flow rate in the second pump 19.

The bubbles generated in the blood product in the warming device 11 are collected in the bubble removal chamber 12. The blood product and the gas in the bubble removal chamber 12 are partly returned to the liquid container 10 through the fourth flow path 17. The flow rate of a fluid containing bubbles which passes through the fourth flow path 17 is controlled by adjusting the liquid delivery flow rate in the first pump 18. For example, by increasing the liquid delivery flow rate in the first pump 18, the flow rate of the fluid flowing out of the bubble removal chamber 12 into the fourth flow path 17 is increased and, by reducing the liquid delivery flow rate in the first pump 18, the flow rate of the liquid flowing out of the bubble removal chamber 12 into the fourth flow path 17 is reduced.

According to the present embodiment, each of the heaters 61 supplies a large amount of heat to the upstream portion of the warming flow path 40 in which the low-temperature blood product flows to allow the amount of heat generation to be gradually reduced with approach to the downstream side in the warming flow path 40. This allows the temperature of the heat plate 60 to approach the upper limit temperature of the blood product throughout substantially the entire region of the warming flow path 40 and consequently allows the blood product flowing in the warming flow path 40 to be efficiently warmed rapidly. In addition, since the amount of heat generation from the heater 61 gradually decreases with approach to the downstream side in the warming flow path 40, the temperature of the heat plate 60 can be controlled not to exceed the upper limit temperature of the blood product. As a result, even when, e.g., the liquid delivery of the blood product is stopped in the warming flow path 40, it is possible to inhibit the blood product from exceeding the upper limit temperature thereof due to heat from the heat plate 60.

Since each of the heaters 61 is the continuous heating wire and the amount of heat generation Q is caused to decrease from the upstream side toward the downstream side in the warming flow path 40 by varying the density or resistance of the heating wire, it is possible to easily and inexpensively adjust the amount of heat generation from the heater 61. Note that the heating wire may be either continuous or divided into a plurality of sections.

In the upstream portion of the warming flow path 40 closer to the inlet port thereof (reciprocating paths 50 to 52), the heaters 61 are disposed along the warming flow path 40 to allow the low-temperature blood product flowing in the upstream portion of the warming flow path 40 to be efficiently warmed. Note that the upstream portion closer to the inlet port refers to the whole or a part of the portion of the warming flow path 40 which is closer to the inlet port than a middle point therein. It may also be possible that, throughout the entire region of the warming flow path 40, the heaters 61 are disposed along the warming flow path 40.

The warming flow path 40 has a structure in which the plurality of reciprocating paths 50 to 55 are laterally arranged and coupled together. The most upstream reciprocating path 50 of the warming flow path 40 includes the plurality of regions R1, R2, and R3 along the warming flow path 40, and each of the heaters 61 is disposed such that the amount of heat generation Q toward the most upstream reciprocating path 50 in the plurality of regions R1 to R3 decreases from the upstream region R1 toward the downstream region R3. This allows the low-temperature blood product flowing most upstream in the warming flow path 40 to be efficiently warmed. The number of regions including the most upstream reciprocating path may be other than 3, i.e., 2, 4, 5, 6, 7, 8, 9, 10, 11, 12, 13, 14, 15, or the like.

Also, in the present embodiment, the heater 61 in the regions R1 to R6, which is at least a part of the heater 61, is disposed along the reciprocating paths 50 to 54 of the warming flow path 40. As a result, heat from the heater 61 is directly and efficiently transmitted to the warming flow path 40 to allow the blood product to be efficiently warmed. In addition, it is possible to inhibit, e.g., heat from staying in the portion of the heat plate 60 without the warming flow path 40 and entering the warming flow path 40. As a result, even when the liquid delivery of the blood product is stopped in the warming flow path 40, it is possible to inhibit the blood product from exceeding the upper limit temperature thereof due to the heat that has flown therein from the portion of the heat plate 60 without the warming flow path 40.

Figure 9:
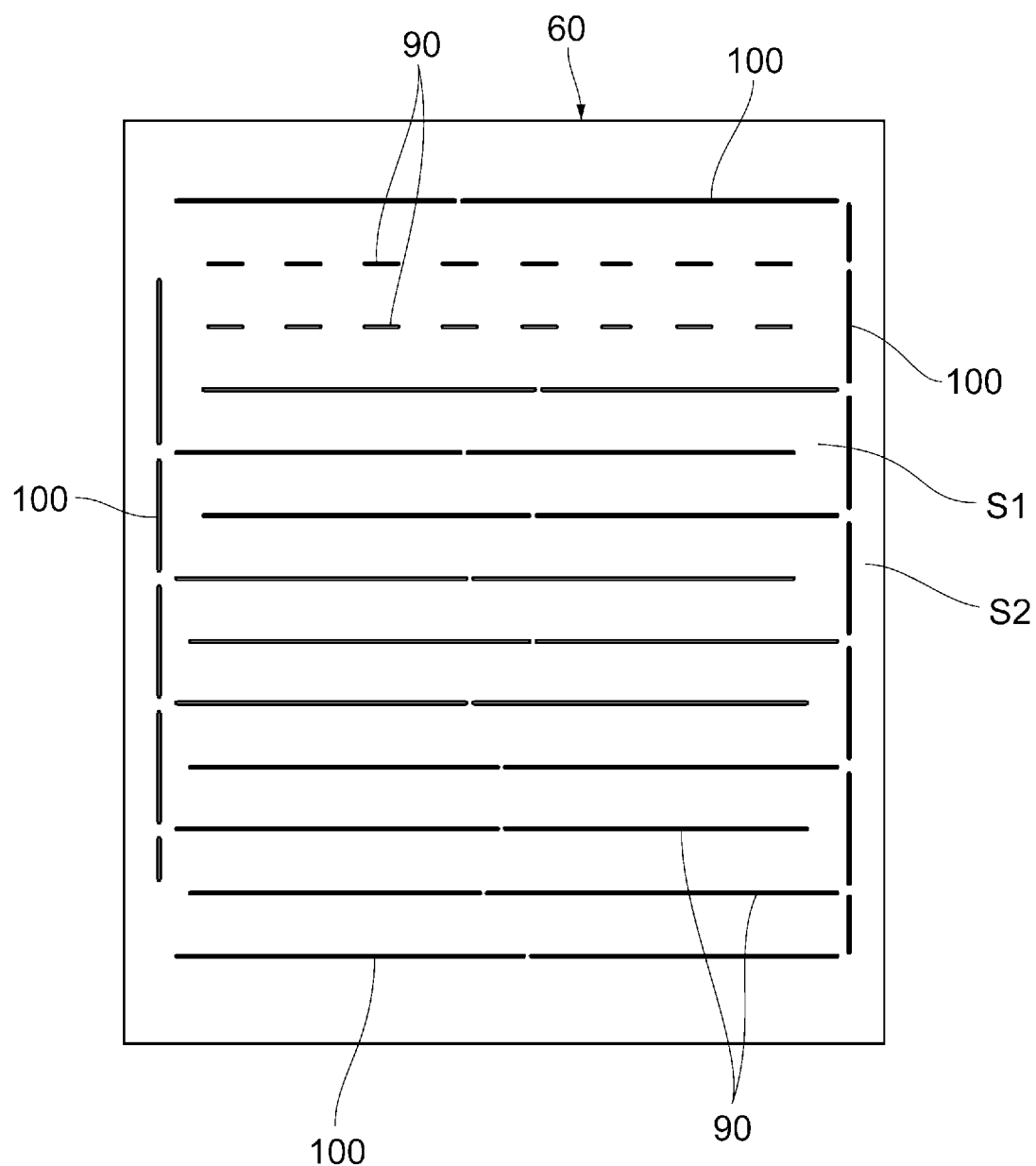
FIG. 9 is an illustrative view showing the heat plate with slits.

In the foregoing embodiment, as shown in FIG. 9, each of the heat plates 60 may also be provided with slits 90 which inhibit heat transmission between the respective regions of the heat plate 60 where the flow paths adjacent to each other in the warming flow path 40 are individually disposed. For example, as shown in FIG. 10, the slits 90 are provided at positions corresponding to the spaces between the outgoing paths and the incoming paths included of all the reciprocating paths 50 to 55 which are adjacent to each other.

Figure 10:
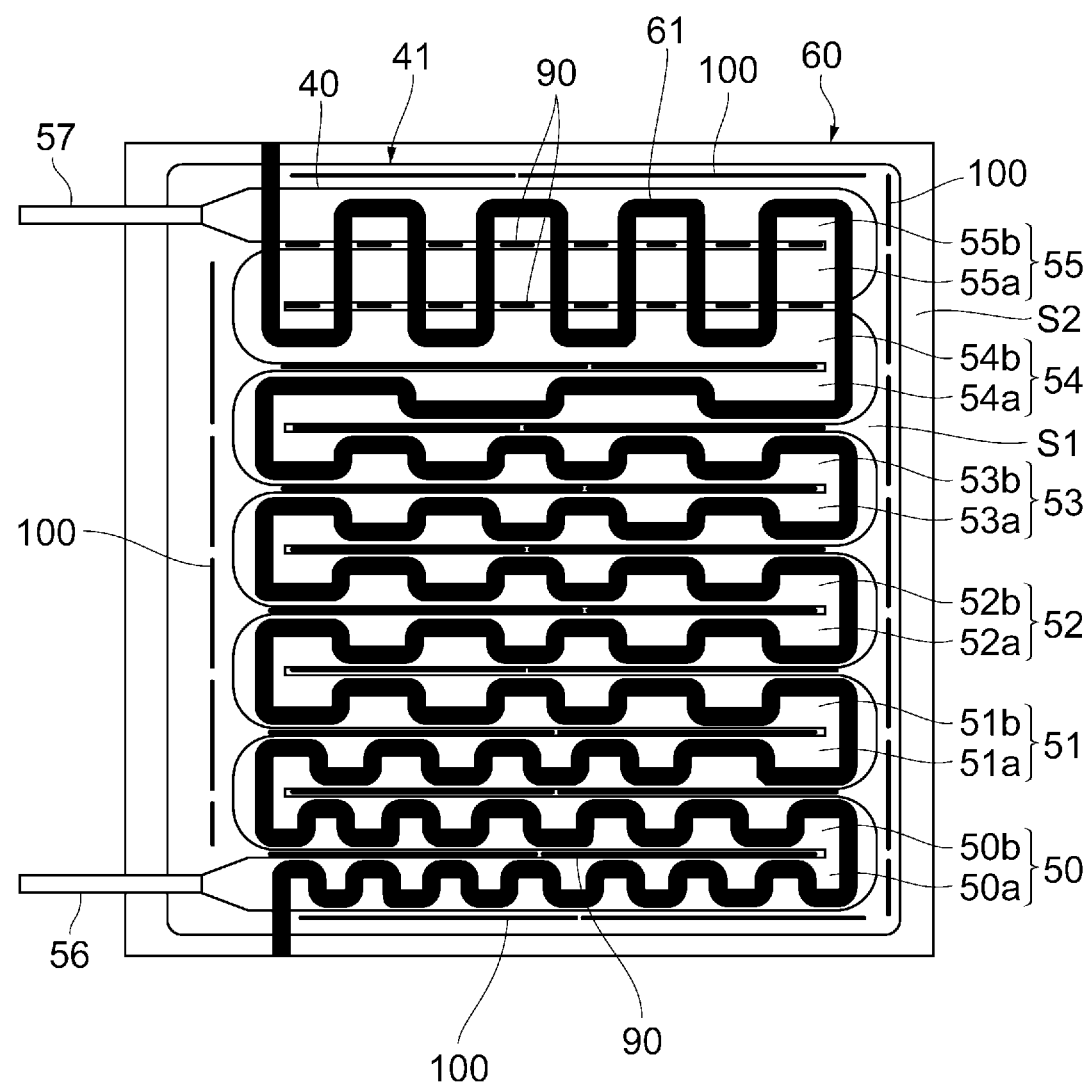
FIG. 10 is an illustrative view showing the positional relationship among the slits, the warming flow path, and the heater.

Alternatively, as shown in FIGS. 9 and 10, each of the heat plates 60 may also be provided with slits 100 which inhibit heat transmission between a region S1 where the heater 61 is disposed and another region S2. In such a case, the slits 100 are disposed, e.g., between the square region S1 of the heat plate 60 where the heater 61 is disposed and the outer peripheral region S2 thereof around the square region S1.

Each of the slits 90 and 100 is discretely formed and has connecting portions included therein. The number of the connecting portions may be one or plural. Since the connecting portions inhibit heat transfer through the connecting portions, the connecting portions may also be located at positions as far away as possible from each of the heaters 61. Each of the slits 90 and 100 is disposed so as not to overlap, e.g., the position where each of the heaters 61 is located. Each of the slits 90 and 100 may be formed in a bottomed groove shape or may extend through the heat plate 60.

According to these examples, the slits 90 can inhibit heat transmission between respective heat plate regions where the flow paths adjacent to each other in in the warming flow path 40 are individually disposed. Consequently, it is possible to strictly control the temperatures of the individual reciprocating paths 50 to 55 of the warming flow path 40. On the other hand, the slits 100 can inhibit heat from each of the heat plates 60 from being diffused from the region S1 with the heater 61 into the region S2 without the heater 61 and inhibit heat in the region S2 without the heater 61 from entering the region S1 with the heater 61. Consequently, it is possible to strictly control the temperature of the warming flow path 40 which is warmed by the heater 61. Note that, in these examples, the heat plate 60 may also be formed with only either the slits 90 or the slits 100. Instead of the slits 90 and 100, a material having a heat insulating property higher than that of the heat plate 60 may also be embedded in holes formed in the heat plate 60 to inhibit heat transmission.

In the present embodiment, it may also be possible that the amount of heat generation Q from each of the heaters 61 exponentially decreases from the upstream side toward the downstream side along the warming flow path 40. In such a case, the blood product can be warmed more efficiently. The case where the amount of heat generation from each of the heaters exponentially decreases when the amount of heat generation decreases in stages from the upstream side toward the downstream side in the warming flow path refers herein to the case where the approximate curve of an exponent function can be drawn so as to pass through the respective upstream ends of the individual stages or the case where the respective upstream ends of the individual stages lie on one exponent function, as shown in FIG. 7.

Second Embodiment

In the foregoing first embodiment, each of the heaters 61 is disposed such that the amount of heat generation Q toward the warming flow path 40 decreases in stages from the upstream side toward the downstream side in the warming flow path 40. However, each of the heaters 61 may also be disposed such that the amount of heat generation Q toward the warming flow path 40 decreases from the upstream side toward the downstream side in the warming flow path and that, when the warming flow path 40 is equally divided into three or more regions along the flow path, the decrease rate of the amount of heat generation Q decreases from the upstream region toward the downstream region.

Figure 11:
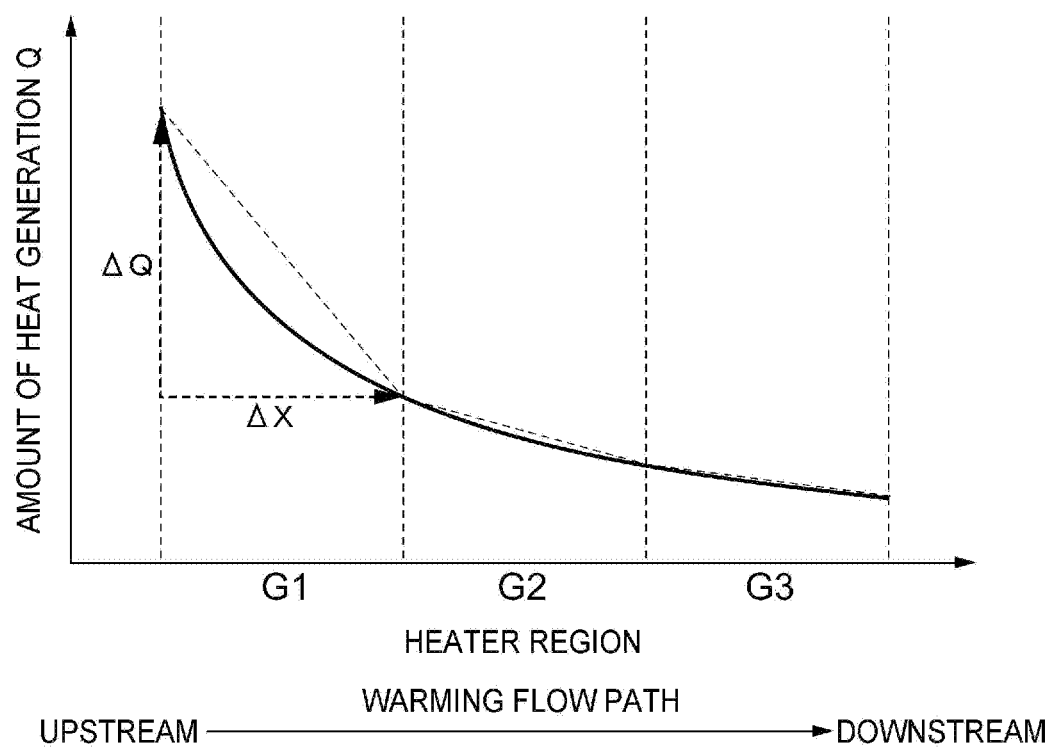
FIG. 11 is a graph showing an example of the relationship between the amount of heat generation from the heater and the warming flow path.

For example, as shown in FIG. 11, each of the heaters 61 is disposed such that the amount of heat generation (heater power) Q continuously decreases from the upstream side toward the downstream side in the warming flow path 40 and that, when the warming flow path 40 is equally divided into three or more regions along the flow path, the decrease rate of the amount of heat generation Q decreases from the upstream region toward the downstream region. For example, when the warming flow path 40 is equally divided into three regions G1, G2, and G3, decrease rates A1, A2, and A3 of the amount of heat generation Q in the individual regions G1, G2, and G3 satisfy A1>A2>A3. It is assumed herein that each of the decrease rates A1 to A3 of the amount of heat generation Q in the individual regions resulting from the equal division is the inclination ($\Delta Q/\Delta X$) of a straight line (shown as the dotted line in FIG. 11) obtained by determining the amount of heat generation Q at the upstream end and the amount of heat generation Q at the downstream end of each of the regions G1 to G3 and connecting the determined amounts of heat generation Q. The number of the regions into which the warming flow path 40 is equally divided is assumed to be three or more herein, but such a case where the number of the regions into which the warming flow path 40 is equally divided is 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 may also be considered.

In each of the foregoing examples, each of the heaters 61 may also be disposed such that, e.g., the amount of heat generation Q exponentially decreases from the upstream side toward the downstream side in the warming flow path 40. Specifically, the curve in which the amount of heat generation Q decreases may also be that of an exponent function given by $Q=A \cdot e^{-B \cdot X}$ (where A and B are constants and X is a position in the warming flow path).

Specifically, each of the heaters 61 is disposed along the plurality of reciprocating paths 50 to 55 of the warming flow path 40, as shown in, e.g., FIG. 6. At this time, at least one of the density and resistance (such as width, thickness, or material) of the heating wire of the heater 61 is reduced from the upstream side toward the downstream side in the warming flow path 40, and the decrease rate thereof is further reduced. As a result, the amount of heat generation Q in the regions G1 to G3 decreases from the upstream side toward the downstream side in the warming flow path 40, and the decrease rate thereof also decreases. In this case, it is sufficient for the amount of heat generation Q in each of the regions resulting from the equal division to decrease in the entire region, and the amount of heat generation Q in each of the regions need not constantly decrease within the region and may also be locally constant or locally increase. Preferably, the amount of heat generation Q in each of the regions constantly decreases within the region.

According to the present embodiment, each of the heaters 61 supplies a large amount of heat to the upstream portion of the warming flow path 40 in which the low-temperature blood product flows, and the amount of heat generation can gradually be reduced with approach to the downstream side in the warming flow path 40. This allows the temperature of the heat plate 60 to approach the upper limit temperature of the blood product throughout substantially the entire region of the warming flow path 40 and consequently allows the blood product flowing in the warming flow path 40 to be efficiently warmed rapidly. In addition, since the amount of heat generation from each of the heaters 61 gradually decreases with approach to the downstream side in the warming flow path 40, it is possible to control the temperature of the heat plate 60 such that the upper limit temperature of the blood product is not exceeded. As a result, even when, e.g., the liquid delivery of the blood product is stopped in the warming flow path 40, it is possible to inhibit the blood product from exceeding the upper limit temperature thereof due to heat from the heat plate 60.

In the present embodiment, when the amount of heat generation Q from the heater 61 exponentially decreases from the upstream side toward the downstream side along the warming flow path 40, the blood product can be warmed more efficiently.

Note that, unless particularly mentioned otherwise, a configuration of the infusion system 1, the warming device 11, or the like described in the foregoing first embodiment is also applicable to that in the second embodiment.

Third Embodiment

Figure 12:
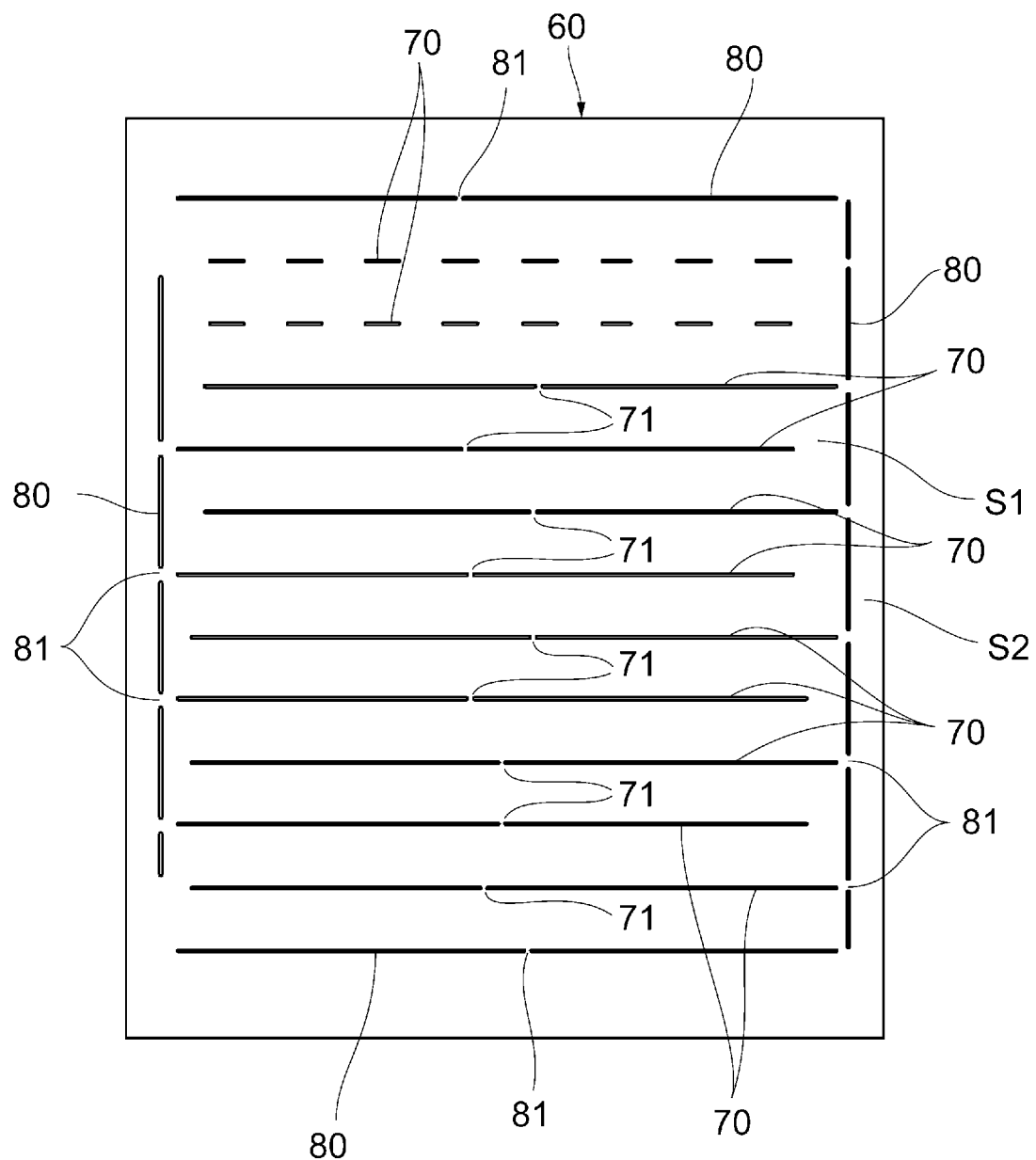
FIG. 12 is an illustrative view showing the slits of the heat plate.
Figure 13:
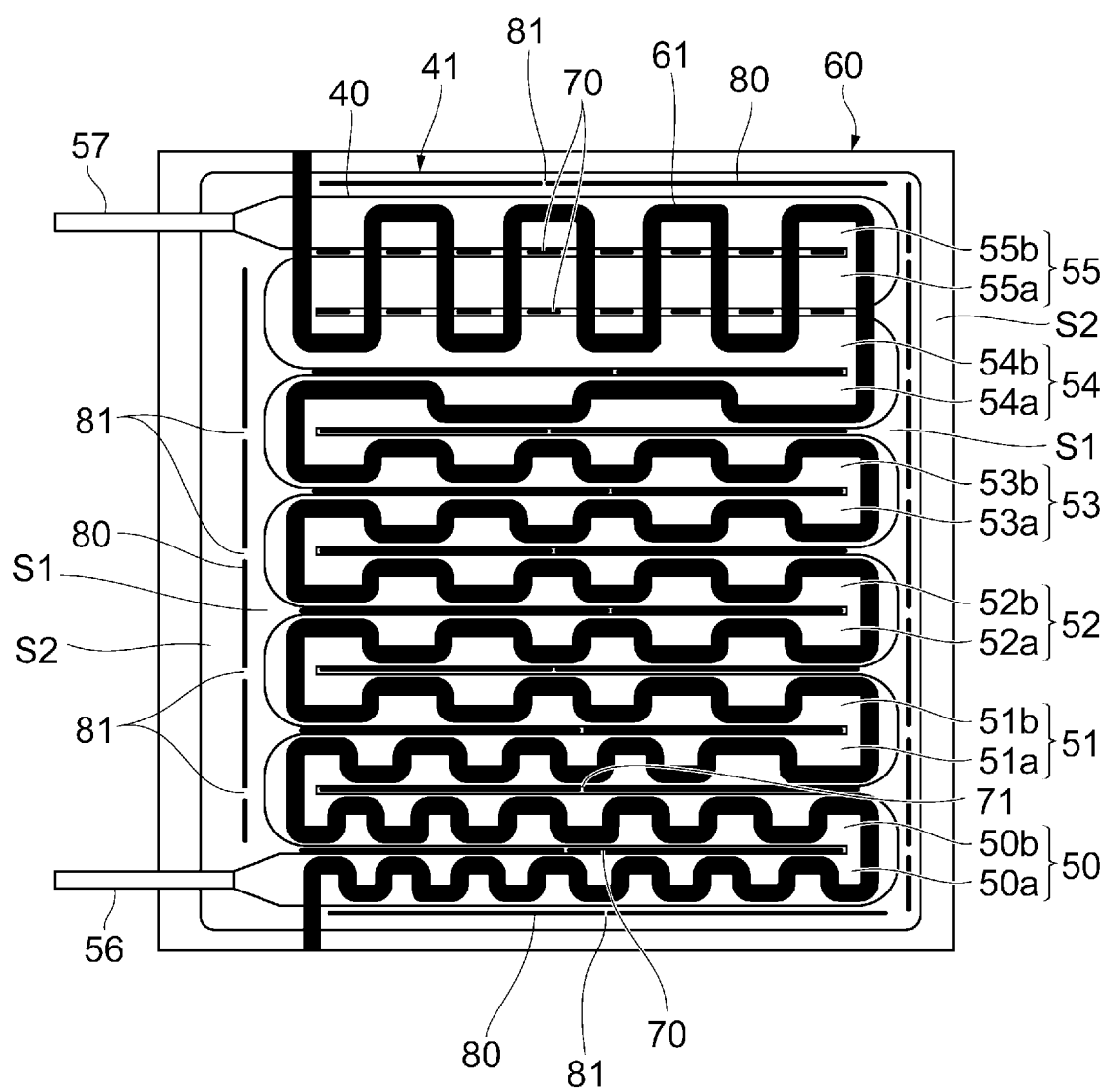
FIG. 13 is an illustrative view showing the positional relationship among the slits, the warming flow path, and the heater.
Figure 14:
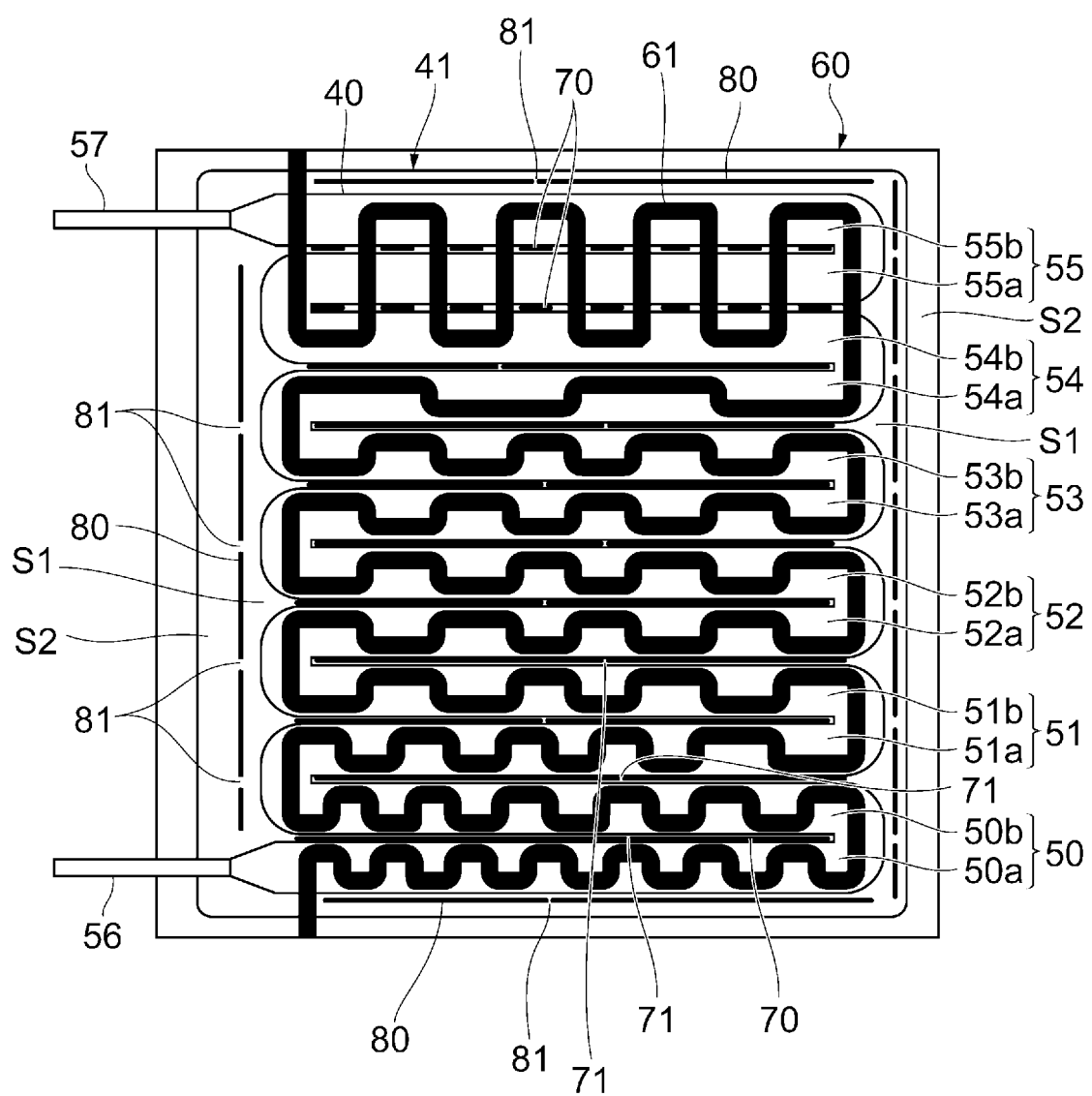
FIG. 14 is an illustrative view showing another example of the layout of the connecting portions of the slits.

A description will be further given of a structure which inhibits heat transmission between the heat plate regions in the foregoing embodiments. FIG. 12 is an illustrative view showing an example of the layout of slits formed in each of the heat plates 60. FIG. 13 is an illustrative view showing the positional relationship among the slits of each of the heat plates 60, the warming flow path 40, and the heater 61. As shown in FIGS. 12 and 13, the heat plate 60 has slits 70 provided as a structure which inhibits heat transmission between the respective heat plate regions where the flow paths adjacent to each other in the warming flow path 40 are individually disposed. For example, as shown in FIG. 13, the slits 70 are provided at positions corresponding to the spaces between the outgoing paths and the incoming paths of all the reciprocating paths 50 to 55 which are adjacent to each other. Accordingly, the slits 70 linearly extend in the directions (lateral directions in FIG. 13) of the outgoing paths and the incoming paths of the reciprocating paths 50 to 55 and are provided to be arranged in parallel in a direction orthogonal thereto (vertical direction in FIG. 13). Each of the slits 70 includes a connecting portion 71 at, e.g., the middle in a longitudinal direction.

As shown in FIGS. 12 and 13, each of the heat plates 60 also has slits 80 provided as a structure which inhibits heat transmission between the region S1 where the heater 61 is disposed and the other region S2. The slits 80 are disposed between, e.g., the square region S1 of the heat plate 60 where the heater 61 is disposed and the outer peripheral region S2 around the square region S1. The slits 80 are formed in linear shapes along the four sides of the outer periphery of the square region S1. Each of the slits 80 is discretely formed and includes a plurality of connecting portions 81.

Figure 15:
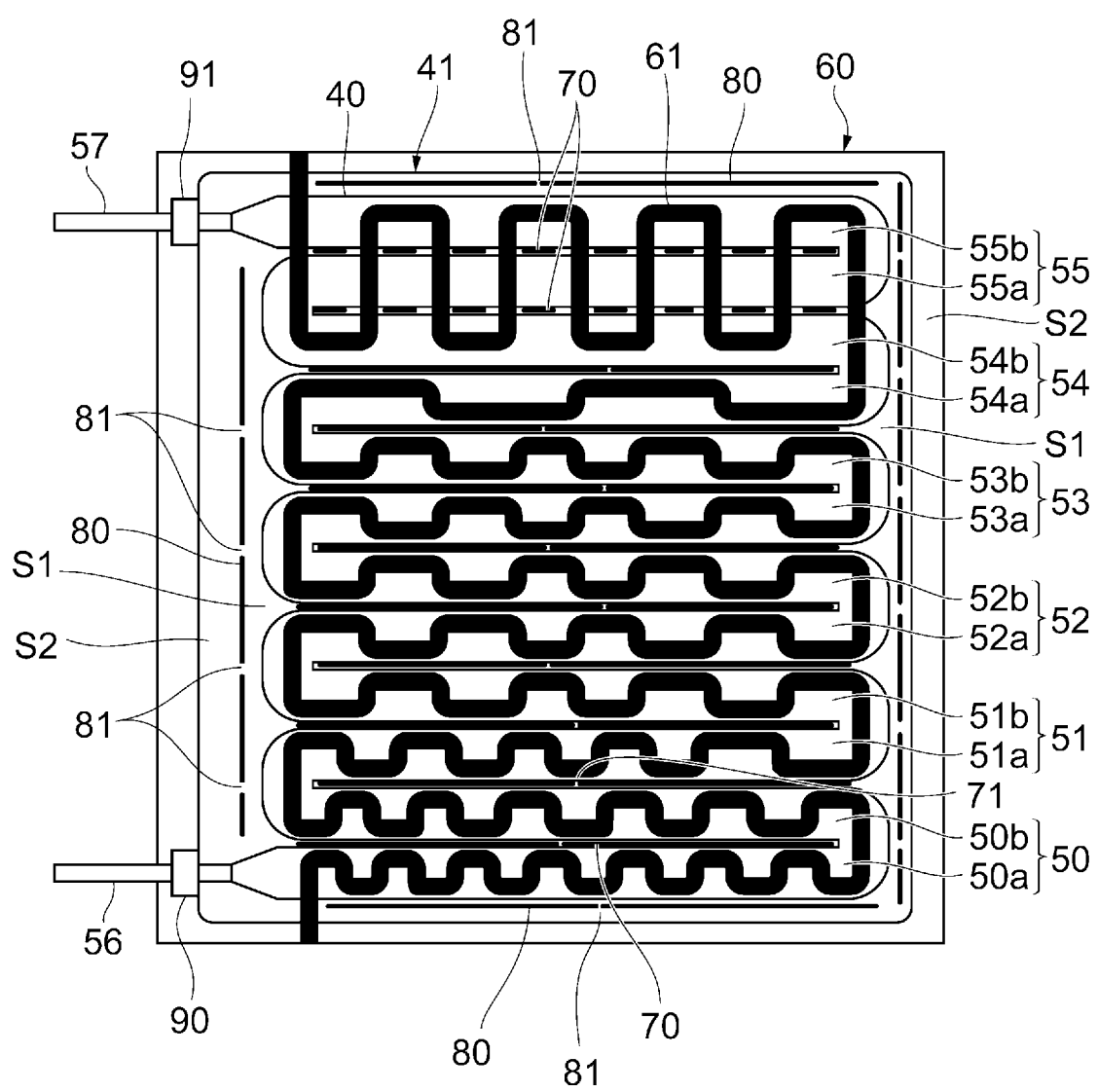
FIG. 15 is a schematic diagram showing respective positions where non-contact-type temperature sensors are provided.

The slits 70 and 80 are disposed so as not to overlap, e.g., the positions where the heaters 61 are located. Each of the slits 70 and 80 may be formed in a bottomed groove shape or may extend through the heat plate 60. To inhibit heat transfer through the connecting portions, each of the connecting portions 71 and 81 may also be disposed in a position as far away as possible from the heater 61, as shown in FIG. 15.

Next, a description will be given of the operation of the infusion system 1 thus configured. First, as shown in FIG. 1, the liquid bag 30 storing therein a low-temperature blood product is connected to the liquid container 10 so that the blood product in the liquid bag 30 is stored in the liquid container 10. Then, the first pump 18 and the second pump 19 are activated to deliver the blood product from the liquid container 10 to the warming device 11 through the first flow path 13. In the warming device 11, the blood product passes through the warming flow path 40, while simultaneously being warmed to a predetermined temperature close to a body temperature by the heat plates 60 using the heaters 61 as a heat source.

At this time, each of the heaters 61 gives heat to the heat plate 60 such that the amount of heat generation decreases from the upstream side toward the downstream side in the warming flow path 40. As a result, in the heat plate 60, a high temperature is retained in a position corresponding to the upstream portion of the warming flow path 40 so that the low-temperature blood product that has entered the warming flow path 40 is efficiently warmed rapidly due to the temperature difference with the heat plate 60. The blood product is warmed to an intended temperature, while flowing in the warming flow path 40. At this time, in the heat plate 60, the slits 70 and 80 inhibit heat transfer in the plane of the heat plate 60.

The blood product warmed in the warming device 11 passes through the second flow path 14 to flow into the bubble removal chamber 12. Then, the blood product is caused by the second pump 19 to pass through the third flow path 16 and be infused from the infusion portion 15 into a patient. The amount of infusion to the patient is controlled by adjusting the liquid delivery flow rate in the second pump 19.

The bubbles generated in the blood product in the warming device 11 are collected in the bubble removal chamber 12. The blood product and the gas in the bubble removal chamber 12 are partly returned to the liquid container 10 through the fourth flow path 17. The flow rate of a fluid containing the gas which passes through the fourth flow path 17 is controlled by adjusting the liquid delivery flow rate in the first pump 18. For example, by increasing the liquid delivery flow rate in the first pump 18, the flow rate of the fluid flowing out of the bubble removal chamber 12 into the fourth flow path 17 is increased. By reducing the liquid delivery flow rate in the first pump 18, the flow rate of the liquid flowing out of the bubble removal chamber 12 into the fourth flow path 17 is reduced.

According to the present embodiment, the slits 70 can inhibit heat transmission between the respective heat plate regions where the flow paths adjacent to each other in the warming flow path 40 are individually disposed. This allows heat from the heater 61 in the regions R1 to R7 to be reliably supplied to the corresponding portions of the warming flow path 40 and allows the blood product to be efficiently warmed.

In addition, the slits 80 inhibit heat from being diffused from the region S1 of the heat plate 60 with the heater 61 into the region S2 of the heat plate 60 without the heater 61 and inhibit heat from entering from the region S2 without the heater 61 into the region S1 with the heater 61. This reduces heat exchange between the heater 61 and the outside thereof and allows the amounts of heat supplied from the heater 61 in the individual regions R1 to R7 to the corresponding portions of the warming flow path 40 to be strictly controlled. In addition, when, e.g., the liquid delivery of the blood product is stopped in the warming flow path 40, it is possible to inhibit heat from flowing from the region S2 without the heater 61 into the region with the heater 61 and excessively warming the blood product in the warming flow path 40. Note that, the heat plate 60 may also be formed with only either the slits 70 or the slits 80.

Since the slits 70 are provided in the positions corresponding to the spaces between the outgoing paths and the incoming paths of the reciprocating paths 50 to 55 which are adjacent to each other, it is possible to appropriately inhibit heat transmission between the adjacent outgoing and incoming paths.

The slit 70, which is provided in the position corresponding to the space between the outgoing path 50a and the incoming path 50b of the most upstream reciprocating path 50 of the warming flow path 40, can strictly control the amount of heat to be supplied to the upstream portion of the warming flow path 40. As a result, it is possible to efficiently warm the low-temperature blood product immediately after flowing into the warming flow path 40.

Figure 16:
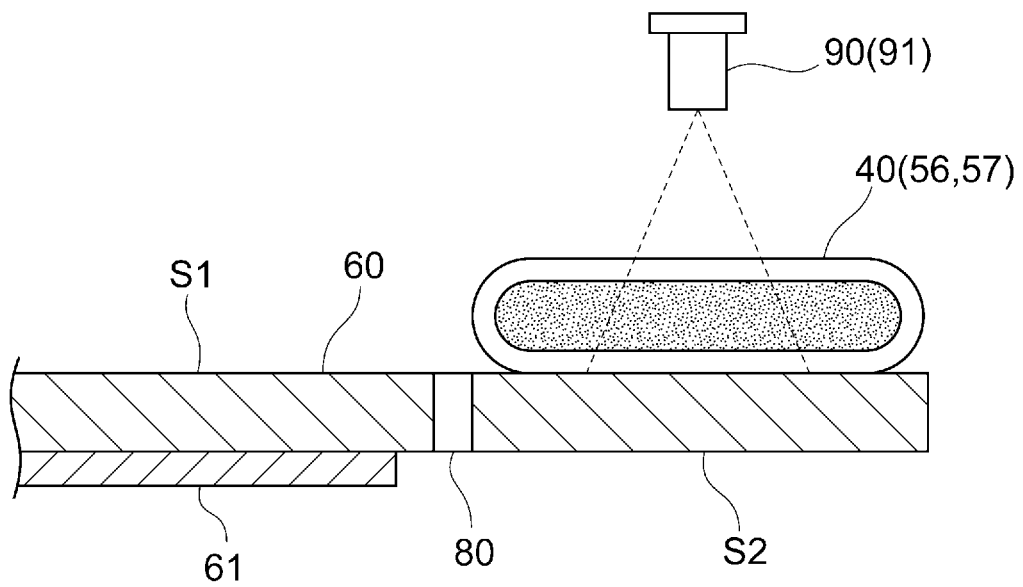
FIG. 16 is a schematic diagram illustrating the measurement of the temperature of a blood product in the warming flow path performed using the non-contact-type temperature sensors.

In the foregoing embodiment, as shown in FIGS. 15 and 16, it may also be possible that, in the region S2 of each of the heat plates 60 without the heater 61, a non-contact-type temperature sensor 90 which measures the temperature of the blood product at the inlet portion 56 of the warming flow path 40 and a non-contact-type temperature sensor 91 which measures the temperature of the blood product at the outlet portion 57 of the warming flow path 40 are provided. In such a case, the non-contact-type temperature sensors 90 and 91 output respective temperature measurement results to the control device 20, and the control device 20 controls the amount of heat generation from each of the heaters 61 on the basis of the temperature measurement results. This allows the temperature of the blood product warmed in the warming flow path 40 to be strictly controlled. In addition, the region S2 where the temperature measurement of the heat plate 60 is performed is separated by the slit 80 from the region R1 with the heater 61, and therefore the region R2 of the heat plate 60 where the temperature measurement is performed is immune to the influence of heat from the heater 61. Consequently, the non-contact-type temperature sensors 90 and 91 are inhibited from sensing, e.g., infrared light radiated from the heat plate 60 and can precisely measure the temperatures of the blood product at the inlet portion 56 and the outlet portion 57.

While the preferred embodiments of the present invention have been described heretofore with reference to the accompanying drawings, the present invention is not limited to these examples. It is obvious that a person skilled in the art can conceive of various modifications or alterations within the scope of the inventive idea defined by the claims, and it is to be understood that, as a matter of course, such modifications or alterations belong to the technical scope of the present invention.

Figure 17:
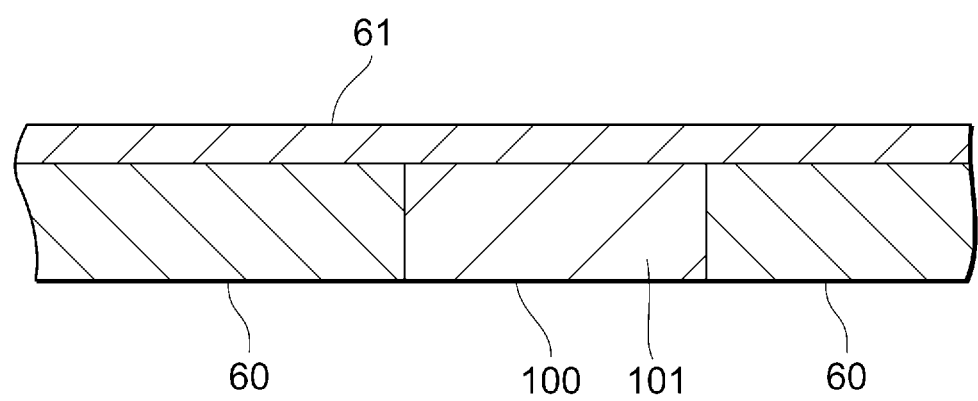
FIG. 17 is an illustrative view showing an example of another structure which inhibits heat transmission.

For example, in the foregoing embodiments, the structure that inhibits heat transmission between the respective heat plate regions where the flow paths adjacent to each other in the warming flow path 40 are individually disposed is the slits 70, while the structure that inhibits heat transmission between the region S1 where the heater 61 is disposed and the other region S2 is the slits 80, but the structures are not limited thereto. For example, as shown in FIG. 17, it may also be possible to fill holes 100 formed similarly to the slits 70 and 80 in each of the heat plates 60 with a material 101 having a heat insulating property higher than that of the heat plate 60. As the material 101 having the higher heat insulating property, e.g., an adhesive used to bond the heaters 61 to the heat plates 60 may be used or a material resulting from the melting of each of the heaters 61 when the heaters 61 are welded to the heat plates 60 may also be used.

The predetermined pattern of each of the heaters 61 in the warming device 11 is not limited to the foregoing example. The number of the regions into which the heater 61 is divided is not limited to seven, and any number can selectively be used. The positions of the boundaries between the regions into which the heater 61 is divided can also be chosen arbitrarily. The number and shapes of the reciprocating paths of the warming flow path 40 are also not limited to those shown above. In the embodiments described heretofore, the heaters 61 of the warming device 11 are provided on both sides of the warming flow path 40, but the heater 61 may also be provided only on one side of the warming flow path 40, as shown in FIG. 18. Specifically, it may also be possible that the heat supply portion 42 and the heat insulating portion 43 are provided on one side of the warming portion 41 having the warming flow path 40, while the heat insulating portion 43 is provided on the other side thereof. The liquid to be infused which is delivered in the infusion system 1 is the blood product, but is not limited thereto. For example, the liquid to be infused which is delivered in the infusion system 1 may also be a fresh frozen plasma (FFP), albumin, or an extracellular liquid.

INDUSTRIAL APPLICABILITY

The present invention is useful in providing a warming device and an infusion system which can efficiently warm a liquid to be infused and also inhibit a liquid in a warming flow path from exceeding the upper limit temperature thereof when the delivery of the liquid is stopped.

REFERENCE SIGNS LIST

1 Infusion system
11 Warming device

40 Warming flow path
41 Warming portion
42 Heat supply portion
50 to 55 Reciprocating path
60 Heat plate
61 Heater
R1 to R7 Region

What is claimed is:

1. A warming device which warms a liquid to be infused, the warming device comprising:
   a warming flow path in which the liquid flows; and
   a heat plate which is in contact with the warming flow path to supply heat to the warming flow path, wherein,
   on the heat plate, a heater in a predetermined pattern corresponding to the warming flow path is disposed, and
   the heater is disposed such that:
      an amount of heat generation toward the warming flow path decreases in consecutive stages from an upstream side toward a downstream side in the warming flow path,
      the consecutive stages include a first stage, a second stage, a third stage, and a fourth stage in consecutive order from the upstream side toward the downstream side, and
      a decrease rate of the amount of heat generation from the first stage to the second stage is greater than the decrease rate of the amount of heat generation from the second stage to the third stage, and the decrease rate of the amount of heat generation from the second stage to the third stage is greater than the decrease rate of the amount of heat generation from the third stage to the fourth stage.

2. A warming device which warms a liquid to be infused, the warming device comprising:
   a warming flow path in which the liquid flows; and
   a heat plate which is in contact with the warming flow path to supply heat to the warming flow path, wherein,
   on the heat plate, a heater in a predetermined pattern corresponding to the warming flow path is disposed, and
   the heater is disposed such that:
      an amount of heat generation toward the warming flow path decreases in consecutive stages from an upstream side toward a downstream side in the warming flow path,
      the consecutive stages include a first stage, a second stage, a third stage, and a fourth stage in consecutive order from the upstream side toward the downstream side,
      a decrease rate of the amount of heat generation from the first stage to the second stage is greater than the decrease rate of the amount of heat generation from the second stage to the third stage, and the decrease rate of the amount of heat generation from the second stage to the third stage is greater than the decrease rate of the amount of heat generation from the third stage to the fourth stage, and
      when the warming flow path is equally divided into three or more regions along the warming flow path, the decrease rate of the amount of heat generation decreases from an upstream region toward a downstream region.

3. The warming device according to claim 1 or 2, wherein the heater is disposed such that the amount of heat generation exponentially decreases from the upstream side toward the downstream side along the warming flow path.

4. The warming device according to claim 1 or 2, wherein the heater is a heating wire.

5. The warming device according to claim 4, wherein the amount of heat generation from the heater decreases from the upstream side toward the downstream side in the warming flow path by varying a density of the heating wire.

6. The warming device according to claim 4, wherein the amount of heat generation from the heater decreases from the upstream side toward the downstream side in the warming flow path by varying a resistance of the heating wire.

7. The warming device according to claim 1 or 2, wherein, in at least an upstream portion of the warming flow path closer to an inlet port thereof, the heater is disposed along the warming flow path.

8. The warming device according to claim 1 or 2, wherein
   the warming flow path has a structure in which a plurality of reciprocating paths each include an outgoing path and an incoming path that are laterally arranged and coupled together,
   the most upstream reciprocating path of the plurality of reciprocating paths has a plurality of regions along the warming flow path, and
   the heater is disposed such that the amount of heat generation toward the plurality of regions of the most upstream reciprocating path decreases from an upstream region at the upstream side toward a downstream region at the downstream side.

9. A warming device which warms a liquid to be infused, the warming device comprising:
   a warming flow path in which the liquid flows; and
   a heat plate which is in contact with the warming flow path to supply heat to the warming flow path, wherein,
   on the heat plate, a heater in a predetermined pattern corresponding to the warming flow path is disposed,
   the warming flow path has a structure in which a plurality of reciprocating paths each including an outgoing path and an incoming path are laterally arranged and coupled together,
   at least a portion of the heater is disposed along the reciprocating path of the plurality of reciprocating paths, and
   the heater is disposed such that:
      an amount of heat generation toward the warming flow path decreases in consecutive stages from an upstream side toward a downstream side in the warming flow path,
      the consecutive stages include a first stage, a second stage, a third stage, and a fourth stage in consecutive order from the upstream side toward the downstream side, and
      a decrease rate of the amount of heat generation from the first stage to the second stage is greater than the decrease rate of the amount of heat generation from the second stage to the third stage, and the decrease rate of the amount of heat generation from the second stage to the third stage is greater than the decrease rate of the amount of heat generation from the third stage to the fourth stage.

10. The warming device according to claim 9, wherein the heater is disposed along at least the most upstream reciprocating path of the plurality of reciprocating paths.

11. The warming device according to claim 9 or 10, wherein
   at least the most upstream reciprocating path of the plurality of reciprocating paths has a plurality of regions along the warming flow path, and
   the heater is disposed such that an amount of heat generation toward the plurality of regions of the most upstream reciprocating path decreases from an upstream region toward a downstream region.

12. The warming device according to any one of claims 1, 2 and 9, wherein the heat plate is provided with a first slit which inhibits heat transmission between respective regions of the heat plate where adjacent flow paths in the warming flow path are individually disposed.

13. The warming device according to claim 12, wherein the heat plate is provided with a second slit which inhibits heat transmission between a region of the heat plate where the heater is disposed and another region of the heat plate.

14. The warming device according to any one of claims 1 and 2, wherein
   the heat plate is provided with a first slit which inhibits heat transmission between respective regions of the heat plate where adjacent flow paths in the warming flow path are individually disposed, and
   the warming flow path has a structure in which a plurality of reciprocating paths each include an outgoing path and an incoming path that are laterally arranged and coupled together, and
   the first slit is provided in a position corresponding to a space between at least one adjacent pair of the outgoing path and the incoming path of the plurality of reciprocating paths.

15. The warming device according to claim 14, wherein the first slit is provided in a position corresponding to a space between the outgoing path and the incoming path of at least the most upstream reciprocating path of the plurality of reciprocating paths.

16. The warming device according to claim 13, wherein, in the other region of the heat plate, at least one of a non-contact-type temperature sensor which measures a temperature of an inlet portion of the warming flow path and a non-contact-type temperature sensor which measures a temperature of an outlet portion of the warming flow path is provided.

17. An infusion system comprising the warming device according to any one of claims 1, 2 and 9.

* * * * *